United States Patent
Çakmak et al.

(10) Patent No.: US 11,247,047 B2
(45) Date of Patent: Feb. 15, 2022

(54) ELECTRO-STIMULATION SYSTEM FOR MUSCLE LOCATION IDENTIFICATION AND THERAPEUTIC RESPONSE ENHANCEMENT

(71) Applicant: STOPARKINSON HEALTHCARE SYSTEMS LLC, Fort Lauderdale, FL (US)

(72) Inventors: Yusuf Ozgur Çakmak, Istanbul (TR); Hakan Urey, Istanbul (TR); Burak Ozsoy, Istanbul (TR); Selim Olcer, Istanbul (TR)

(73) Assignee: STOPARKINSON HEALTHCARE SYSTEMS, LLC, Fort Lauderdale, FL (US)

( * ) Notice: Subject to any disclaimer, the term of this patent is extended or adjusted under 35 U.S.C. 154(b) by 602 days.

(21) Appl. No.: 16/125,416

(22) Filed: Sep. 7, 2018

(65) Prior Publication Data
US 2019/0009087 A1 Jan. 10, 2019

Related U.S. Application Data

(63) Continuation of application No. PCT/TR2016/050064, filed on Mar. 9, 2016.

(51) Int. Cl.
*A61N 1/36* (2006.01)
*A61N 1/05* (2006.01)
(Continued)

(52) U.S. Cl.
CPC .......... *A61N 1/36003* (2013.01); *A61B 5/296* (2021.01); *A61B 5/4836* (2013.01);
(Continued)

(58) Field of Classification Search
None
See application file for complete search history.

(56) References Cited

U.S. PATENT DOCUMENTS 4,067,342 A * 1/1978 Burton ................. A61N 1/0492
607/152
4,112,941 A * 9/1978 Larimore ............... A61B 5/274
600/394
(Continued)

FOREIGN PATENT DOCUMENTS

WO WO 2010/048261 A1 4/2010
WO WO 2014/207512 A1 12/2014

OTHER PUBLICATIONS

International Search Report and Written Opinion, dated Sep. 12, 2016, pp. 1-10, issued in International Application No. PCT/TR2016/050064, European Patent Office, Rijswijk, The Netherlands.
(Continued)

*Primary Examiner* — Shirley X Jian
(74) *Attorney, Agent, or Firm* — Crowell & Moring LLP (57) ABSTRACT

An electro-simulation system includes an electro-stimulation device where the supplementary motor area, premotor area and/or subthalamic nucleus are stimulated extra-cranially. The electro-stimulation device includes at least one electrode, said at least one electrode being provided with a stimulation end configured to be directly attached to intrinsic auricular muscles of a human so as to establish a direct contact relation therewith, said stimulation end being operatively coupled with a sensor.

31 Claims, 3 Drawing Sheets

(51) Int. Cl.
    *A61B 5/00*         (2006.01)
    *A61B 5/296*      (2021.01)
    *A61N 1/04*         (2006.01)
    *A61N 1/372*       (2006.01)

(52) U.S. Cl.
    CPC ....... *A61N 1/0526* (2013.01); *A61N 1/36036* (2017.08); *A61N 1/36067* (2013.01); *A61N 1/0452* (2013.01); *A61N 1/37235* (2013.01)

(56) References Cited

U.S. PATENT DOCUMENTS

| | | | |
|---|---|---|---|
| 5,514,175 | A | 5/1996 | Kim et al. |
| 5,707,396 | A | 1/1998 | Benabid |
| 8,761,872 | B2* | 6/2014 | Hinrichsen ........ A61N 1/36017 607/2 |
| 9,415,220 | B1* | 8/2016 | Spinelli .............. A61N 1/36036 |
| 9,782,584 | B2* | 10/2017 | Cartledge ............ A61N 1/0472 |
| 9,855,426 | B2 | 1/2018 | Cakmak et al. |
| 10,279,178 | B2* | 5/2019 | Cartledge .......... A61N 1/36036 |
| 2008/0249594 | A1 | 10/2008 | Dietrich et al. |
| 2010/0094377 | A1 | 4/2010 | Graupe |
| 2010/0114191 | A1* | 5/2010 | Newman ................. A61N 7/00 607/3 |
| 2011/0009920 | A1 | 1/2011 | Whitehurst et al. |
| 2011/0046432 | A1* | 2/2011 | Simon ..................... A61N 2/02 600/14 |
| 2013/0079862 | A1 | 3/2013 | Ellrich |
| 2013/0296987 | A1* | 11/2013 | Rogers .................... A61F 7/007 607/112 |
| 2013/0310907 | A1* | 11/2013 | Rogers .................. A61N 2/002 607/113 |
| 2014/0357975 | A1* | 12/2014 | Nesbitt .................. A01N 59/20 600/396 |
| 2014/0358010 | A1* | 12/2014 | Battiwalla ............. A61B 5/486 600/476 |
| 2015/0112405 | A1 | 4/2015 | Brown et al. |
| 2015/0360030 | A1* | 12/2015 | Cartledge .......... A61N 1/36036 607/60 |
| 2017/0087364 | A1* | 3/2017 | Cartledge ............ A61N 1/3603 |
| 2018/0021564 | A1* | 1/2018 | Goodall ............... A61N 1/0541 600/379 |
| 2020/0261722 | A1* | 8/2020 | Alataris ............... A61N 5/0603 |
| 2020/0345970 | A1* | 11/2020 | La Rovere ........... A61N 1/0456 |

OTHER PUBLICATIONS

International Preliminary Report on Patentability, dated Jul. 5, 2018, pp. 1-20, issued in International Application No. PCT/TR2016/050064, European Patent Office, Munich, Germany.

* cited by examiner

ELECTRO-STIMULATION SYSTEM FOR MUSCLE LOCATION IDENTIFICATION AND THERAPEUTIC RESPONSE ENHANCEMENT

RELATED APPLICATIONS

The present patent document is a continuation of International PCT Application Serial No. PCT/TR2016/050064, filed Mar. 9, 2016, designating the United States and published in English, which is hereby incorporated by reference.

BACKGROUND

1. Technical Field

The present disclosure relates to an electro-stimulation device where the supplementary motor area, premotor area, cerebellum and/or subthalamic nucleus are stimulated.

2. Background

Abnormal resting over activity as tremors can be caused by various conditions or medicines that affect the nervous system, including Parkinson's disease (PD), liver failure, alcoholism, mercury or arsenic poisoning, lithium, and certain antidepressants. Rigidity, bradykinesia and postural instability are some of the other symptoms of the Parkinson's disease besides tremors. Parkinson's disease is a chronic and progressive movement disorder, meaning that symptoms continue and worsen over time. According to European Parkinson's Disease Association, it is estimated that 6.3 million people in the world are living with Parkinson's disease. The cause is unknown, and although there is presently no cure, there are treatment options such as medication and surgery to manage its symptoms. Stimulation of different parts of a brain with different technics can be successfully used for the treatment of Parkinson's disease.

SUMMARY

The main objectives of the deep brain stimulation (DBS) devices are stimulation of the subthalamic nucleus and as a consequence, activation of the supplementary motor areas and premotor areas and normalization of the abnormal resting over activity in the motor system.

Subthalamic Nucleus-Deep Brain Stimulation (STN-DBS) is an invasive, but an effective approach to Parkinson's disease (PD) Symptoms. Standard STN-DBS for PD is usually delivered 100 to 250 Hz (130 Hz-185 Hz) with a voltage level of 1-4V and pulse width of 60 microseconds. On the other hand, to achieve specific effects, different frequencies are generally used; for instance while in order for improving swallowing, freezing and axial gait functions 60 Hz is considered effective, 130 Hz is not effective. Moreover, for verbal fluency 60 Hz works better than 130 Hz. On the basis of the available data, it is to be noted that a particular stimulation frequency may be needed for alleviating different symptoms of PD disease. For the tremor resistant patients, the frequency is generally selected as 180 Hz.

Current applications to stimulate subthalamic nucleus includes intracranial electrode placement, which is called deep brain stimulation. The process of deep brain stimulation of the subthalamic nucleus requires a neurosurgery, which is an extremely invasive intervention for the Parkinson's patient. In this neurosurgery operation, electrodes are placed into the subthalamic nucleus region which includes a map of muscles of the human body. The neurons in this muscle map have feedbacks (like stretch, length etc.) from muscles of the human body. In other words to stimulate the STN externally, a nerve which is related with muscle innervation should be stimulated.

Further, surgical device applications are likely to have side effects. Moreover, the battery of the stimulator is placed under the thorax skin while the electrodes inserted into the brain tissue and the wires go under the skin. The frequency and the intensity of these stimulators can be altered wirelessly with an external unit. The U.S. Pat. No. 5,707,396 discloses a method of arresting degeneration of the substantia nigra by high frequency stimulation of subthalamic nucleus. This method needs the electrodes to be neurosurgically implanted into substantia nigra besides surgical implantation of the battery.

Among others, a prior art publication in the technical field may be referred to as U.S. Pat. No. 5,514,175, which discloses a treatment device described as a low voltage, multi-point auricular stimulator for dysfunctions in neural pathways by acting upon multiple auricular points. Another reference can be given as the European patent disclosure EP 2474339, disclosing a resuscitation device for resuscitation by stimulating an auricle of a human ear. Further prior art references in the present technical field can be cited as WO2014207512A1, US 2008/0249594, US 2013/0079862 or WO 2010/048261.

The present disclosure, on the other hand, is directed to an electro-stimulation system that addresses the situation where an extra-cranially placed device not only stimulates but also senses the physical state of the patient and the adequacy and quality of his/her responses to the stimulation effect. It is also to be noted that stimulation of the intrinsic auricular muscles alone is not sufficient for alleviating the Parkinson's disease symptoms. To this end, the electro-stimulation system provides an electrode placed on the intrinsic muscles for effectuating stimulation of the intrinsic auricular muscles in the appropriate frequency combinations to obtain symptom-specific results.

Different techniques provide methods for accurately locating the intrinsic auricular muscles connected to the predefined regions of the brain with neuropath channels. EMG (Electromyography) sensors measure electrical currents/impulses generated in muscles during the contraction thereof and at rest. The electro-stimulation system is designed under the recognition that the collected data by the EMG sensor is used to drive the stimulator and adjust various settings during effecting of the muscle stimulation.

A feature of the electro-stimulation system relates to an electro-stimulation device where the supplementary motor area, premotor area, cerebellum and/or subthalamic nucleus are stimulated extra-cranially by which Parkinson disease, Migraine, movement disorders, depression or pain management can be treated.

Another feature of the electro-stimulation system relates to an electro-stimulation device where the supplementary motor area, cerebellum, premotor area and/or subthalamic nucleus are stimulated via auricular muscles.

Another feature of the electro-stimulation system relates to an electro-stimulation device where the stimulation parameters of the supplementary motor area, cerebellum, premotor area and/or subthalamic nucleus is changed according to the data collected by a plurality of peripheral sensing units.

BRIEF DESCRIPTION OF THE DRAWINGS

The embodiments may be better understood with reference to the following drawings and description. The com- FIG. 1 demonstrates a schematic view of one embodiment of an electro-stimulation device.

FIG. 3 additionally demonstrates an additional electrode (shown by dashed lines) reaching to a fourth intrinsic auricular muscle.

DETAILED DESCRIPTION

The following numerals are referred to in the detailed description:
10) Electro-stimulation device
11) Electrode
12) Stimulation end
13) Insulating sleeve
14) Connection element
15) Receiving portion
16) Enclosure
17) Connection line
18) Magnetic element
19) Magnetic anchoring means
20) Core
21) Control unit
22) Retainment portion
23) Ear-wearable device
24) Retractable connection extension
25) Housing portion
26) Ear-wearable body
27) Sensor The electro-stimulation system is effective in muscle location identification therapeutic response enhancement. The system includes an electro-stimulation device (10) having at least one electrode (11) also having sensing function and a stimulation end (12) of which controlling the stimulation process based on the collected data, also through said electro-stimulation device (10) as will be delineated hereinafter.

The electro-stimulation device (10) provides that fine-tuning of parameters such as current, voltage, polarization, signal form is carried out and the correct needle position (position of the stimulation end (12)) of the electro stimulation device (10) is verified thanks to a sensor (27) operatively coupled to the stimulating end (12) of the electro stimulation device (10). Preferably an EMG sensor (27) is used to fulfill this function; however, other sensing mechanisms such as a current probe or an electro-coil for sensing electrical current can be of use. As is known to the skilled worker, an EMG (Electromyography) sensor (27) measures electrical currents/impulses generated in muscles during the contraction thereof and at rest. The at least one electrode (11) of the electro-stimulation device (10) is adapted to be directly attached to intrinsic auricular muscles such as helicis major muscles, helicis minor muscles, tragicus muscles, anti-tragicus muscles etc.

According to a first alternative embodiment, the electro-stimulation device (10) comprises a connection element (14) which provides a certain parameter signal as a voltage or current signal and preferably in the form of current-amplified signal from a control unit (21) to said at least one electrode (11). The electro-stimulation device (10) is also configured to assume the role of a sensing unit which enables receiving of an electrical signal such as a current signal from a respective muscle during the contraction thereof and at rest in the manner that such data from the respective muscle is used to serve to the purpose of verifying the exact location of the intended muscle as well as adjusting the threshold of a stimulating signal to be applied to said muscle. Therefore, the system ensures that the same electrode (11) of the electro-stimulation device (10) acts as a stimulating and sensing unit as will be explained below.

Accordingly, signals to be sensed and signals effective in stimulation are carried via the same electrodes (11). Different time slots are allocated for signals to be sensed and signals for stimulating; thus multiplexing said signals. In a preferred embodiment of the present application in reference to FIG. 1, said electrodes (11) are configured to be in the form of needle-shaped electrodes (11) as in the case of acupuncture needles. Preferably, each of said electrodes (11) comprises an insulating sleeve (13). Said insulating sleeve (13) surrounds the electrode (11), except for the stimulation end (12) thereof. In this embodiment, electrodes (11) are pricked on the auricular skin and stimulation end (12) of the electrode (11) reaches said intrinsic auricular muscles.

Figure 1:
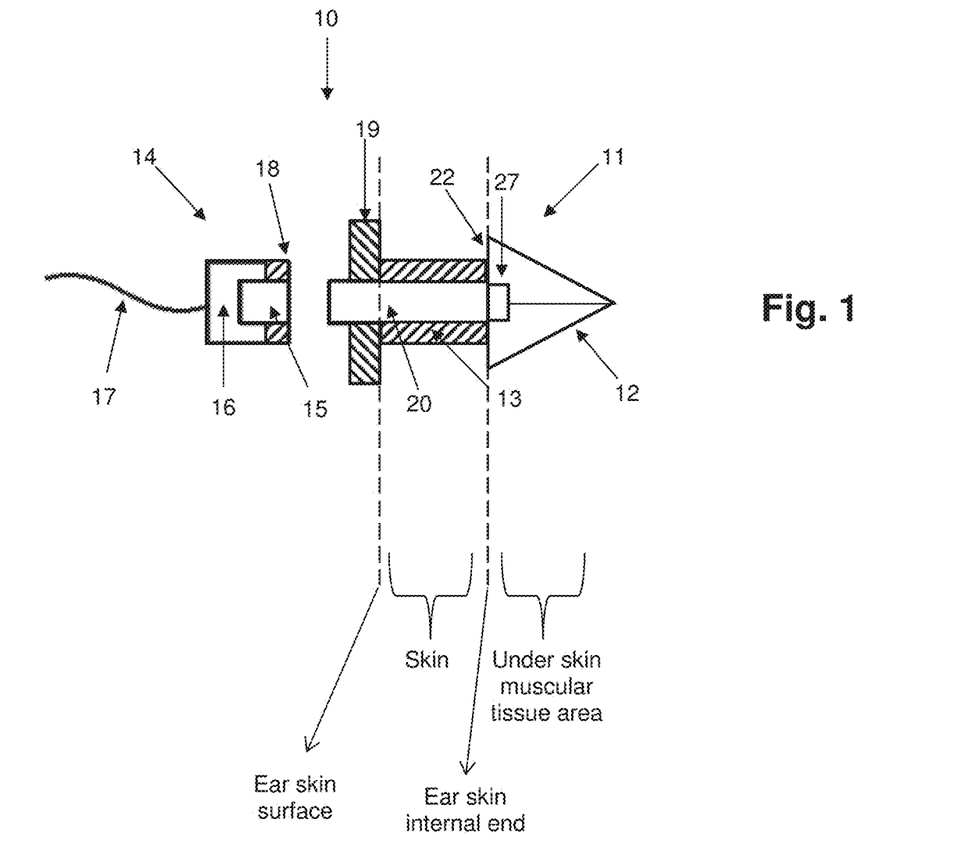

Said insulating sleeve (13) essentially serves to the purpose of preventing signals produced by the control unit (21) from reaching the auricular skin, thus helps ensuring that the signals are directly transmitted to the intrinsic auricular muscles. In other words, only the stimulation end (12) of the electrode (11) conveys the required signal to the intended muscle and the surrounding tissue portions other than the intended recipient portion is not conveyed any stimulation signal, which would otherwise cause a certain amount of irritation for the patient. Further, polarization of the signal being applied can be adjusted to prevent a certain pain sensation at the auricular area by applying positive or negative signals in subsequent cycles.

The system further provides that temperature of the stimulation end (12) is continuously monitored to avoid excessive heating thereof beyond a predetermined limit such that the user is protected from pain sensations in the intrinsic auricular muscles. The stimulation end's (12) initial temperature and temperature thereof at the end of an inactive period indicative of the temperature of the respective intrinsic auricular muscle are monitored and the active state temperature of the stimulation end (12) is intermittently decreased to the local temperature of the respective intrinsic auricular muscle as measured at the end of a predetermined inactive period of the stimulation end (12) before stimulation is initiated.

Preferably, one longitudinal side of said stimulation end (12) away from the same is shaped to be slightly thicker than the insulating sleeve (13). To this end, the stimulation end (12) is provided with an annular flange slightly extending over the cross-sectional area of the tubular-form insulating sleeve (13), which then functions as a retainment portion (22) due to its thicker or larger surface area preventing the stimulation end (12) from disconnecting from the intrinsic auricular muscles when it takes its operational position. In a more specific manner, the ring-shaped flange surface around the tubular body of the insulating sleeve (13) at the base of the stimulation end (12) helps maintaining the operational position of the electrode (11).

Typically, a driving circuit is used in generating stimulating signals. In another preferred embodiment of the present application, said connection elements (14) are detachable from the electrodes (11). The driving circuit preferably communicates with the connection element (14)

such that simulating signals are generated in the stimulating end (12) of the electrode when the latter is connected with the connection element (14). Therefore, the driving circuit together with the control unit (21) is embedded in an external unit of the electro-stimulation device (10).

In this embodiment, the electro-stimulation device (10) comprises at least one connection element (14), which is connected to said driving circuit via a connection line (17) and which is detachably connected to at least one electrode (11) in electrical communication therewith. Said connection element (14) comprises an enclosure (16), preferably also made from an insulating material and a receiving portion (15) suitable for receiving the longitudinally extending core (20) of the electrode (11). Therefore, the stimulating end (12) integral with the core (20), the latter being enclosed by the insulating sleeve (13), cooperates with said receiving portion (15) in the manner that the two parts mate in an interengaged manner. In other words, the core (20) of the electrode (11) is introduced to the receiving portion (15) and this operational position thereof is maintained by a couple of magnetic means, namely a first magnetic element (18) and a magnetic anchoring means (19) as explained hereinafter.

In this embodiment, the electro-stimulation device (10) comprises a magnetic element (18) and a magnetic anchoring means (19), one of which (the magnetic element (18)) is placed on the connection element (14) and the other is placed on the electrode (11). Magnetic element (18) and magnetic anchoring means (19) together ensure that the connection element (14) is securely connected and releasably fixedly attached to the electrode (11).

The magnetic anchoring means (19) is a stationary attachment location to which said magnetic element (18) can be temporarily joined thereto during which the electro-stimulation device (10) operates. Other than this operational state, the magnetic element (18) can be conveniently removed and stored until further use. Therefore, according to this embodiment, the electrodes (11) are implanted to the ear of the patient such that the stimulating end (12) of the electrode (11) remains in connection with the intrinsic auricular muscles. The system therefore affords substantially practical and facilitated use of the electro-stimulation device (10) by patients so as to attach/detach said connection element (14) to the electrode (11) even in the absence of an experienced medical practitioner, paramedic etc.

In reference to FIG. 1, in the operational position, the laterally or radially extended portions of the magnetic anchoring means (19) lean on the ear surface of the user's ear skin and the longitudinal insulting sleeve (13) extension constitutes the under skin region of the skin's outer wall reaching to the muscular tissue area where the stimulation end (12) contacts the auricular muscles. The laterally or radially extended portions of the magnetic anchoring means (19) are dimensionally adapted to retain the depthwise position of the stimulation end (12) at a predetermined level during which further depthwise movement thereof is prevented by said laterally or radially extended portions leaning on the skin.

In one embodiment, the electro-stimulation device (10) comprises an optional system that verifies the location of muscles in auricular area. To this end, thermal and/or pressure sensors may externally determine the exact locations of the muscles. Further, a laser marking system can be used in indicating the determined specific locations where the muscles to be stimulated are positioned.

In a variation, the electro-stimulation device (10) may comprise a system that selectively varies specific operational parameters according to different symptoms in the same session. Generally, while the frequency signal set at 60 Hz cures the voice-related parameters (basically voice quality) of a patient, 130 Hz cures the rigidity and postural instability. Therefore, data collected from a plurality of sensors such as for instance an inertial measurement unit being embodied in peripheral sensing units in signal communication with the control unit (21) of the present electro-stimulation device (10), can be used in selectively applying varying treatment parameters. Likewise, the intensity, speed and for instance swallowing duration etc. of a patient can be analyzed by a speech processing software (preferably real-time or as a pre-treatment recorded sample) and the data collected as such can thereby be used in selectively applying varying treatment parameters as explained above. Different treatment routines with varying frequencies can be subsequently applied in the manner that while a frequency value is adopted for a predetermined time duration, the frequency can be subsequently varied for another predetermined time duration in a symptom-specific manner.

In one embodiment, the electro-stimulation device (10) is mountable to a hearing aid and a more compact assembly functioning as a multi-function unit is obtained.

In one embodiment, the electro-stimulation device (10) comprises at least one communication unit, which enables realizing of communication with other devices. Typically, the control unit (21) enables signals to be sent to/received from electrodes (11), controlling the driving circuit, receiving signals from the stimulating end (12) also acting as a sensing unit and controlling the communication unit.

Figure 2:
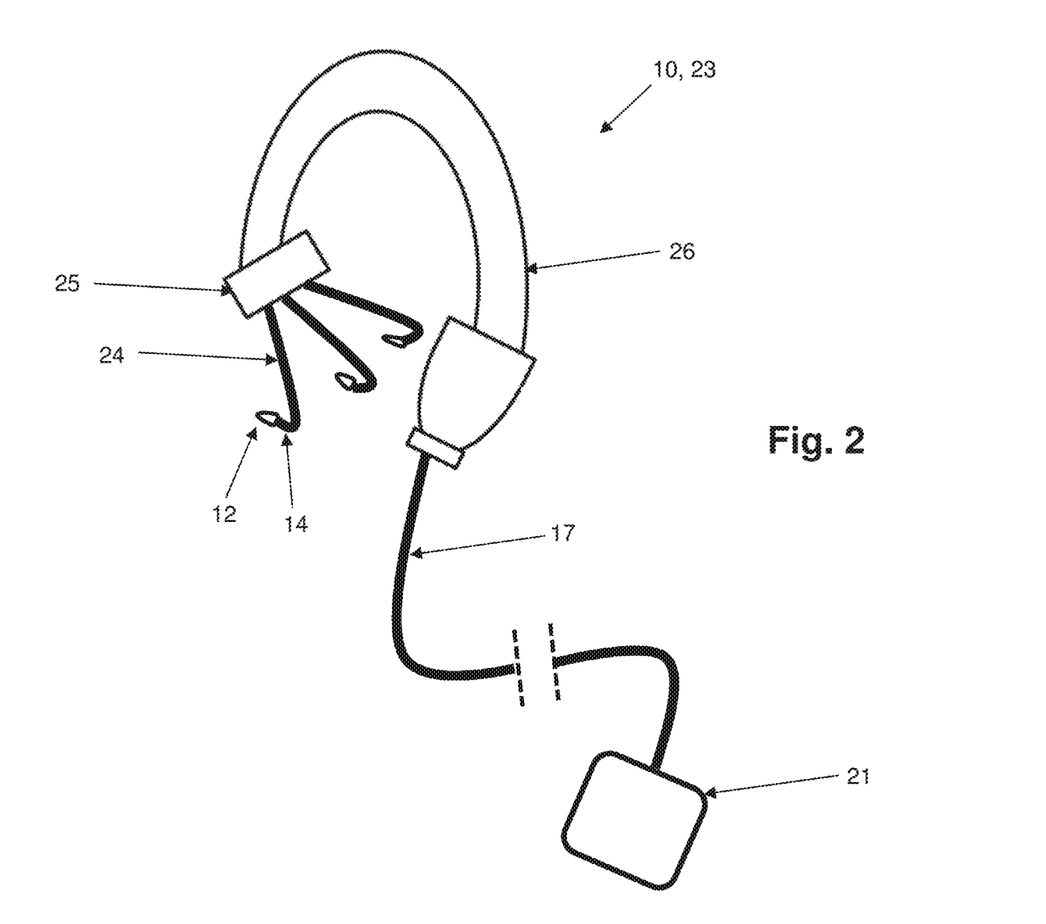
FIG. 2 demonstrates a schematic view of an ear-wearable stimulation device according to an alternative embodiment.
Figure 3:
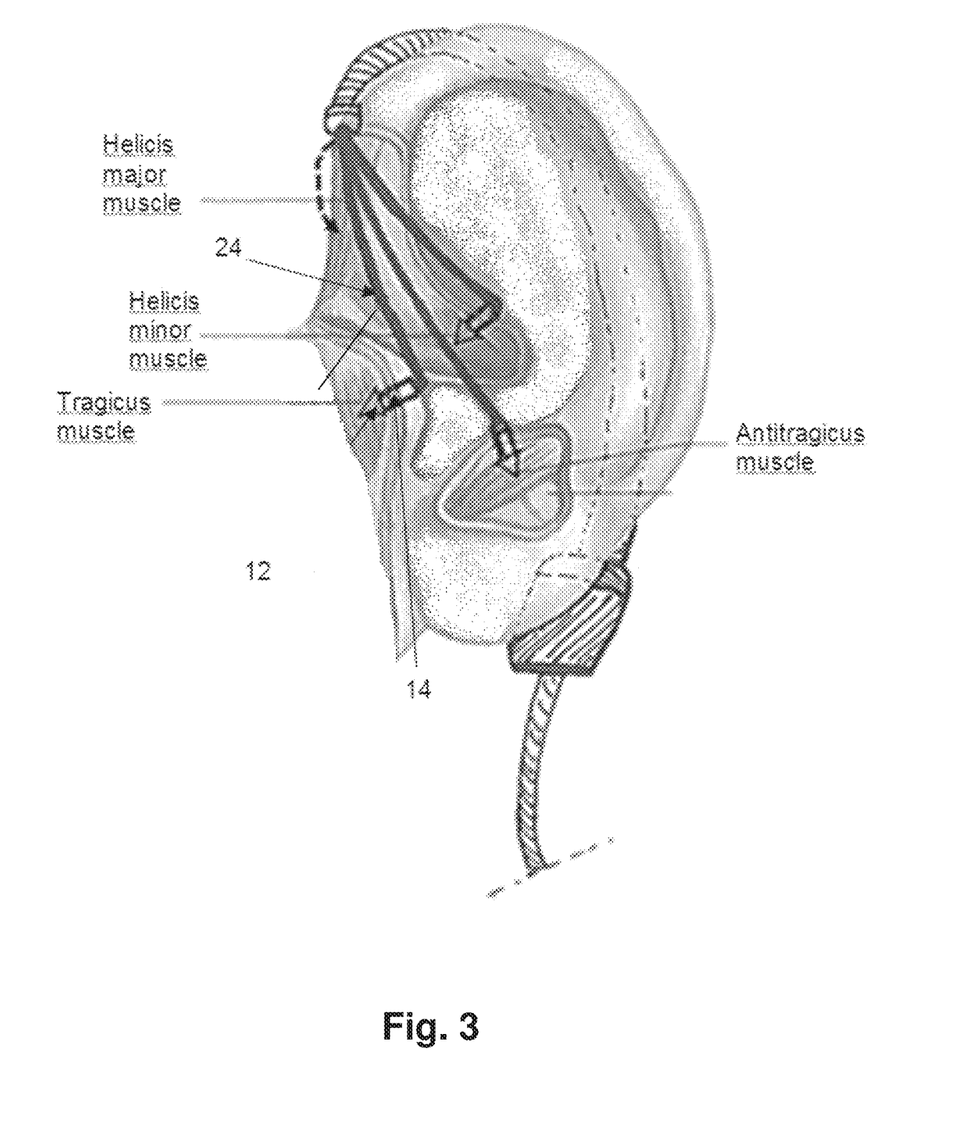
FIG. 3 demonstrates a schematic view of an ear wearable stimulation device with stimulation ends with respect to different position on an actual human ear according to the alternative embodiment of FIG. 2.

In another preferred embodiment, the electro-stimulation device (10) is an ear-wearable device (23) as an external unit with a plurality of stimulating ends (12), each of which being equipped with an EMG sensor (27) operatively coupled thereto. The stimulating ends (12) can be already implanted to target intrinsic auricular muscles such as helicis major muscles, helicis minor muscles, tragicus muscles, anti-tragicus muscles etc. in contact relation while the respective connection elements (14) of the ear-wearable device (23) are releasably couplable to the stimulating ends (12) only during the treatment procedure.

This practical device has flexible and retractable connection extensions (24) to adjust the distance between a connection element (14) releasably connectable with a stimulating end (12) and a housing portion (25) of the ear-wearable device (23), from which portion the components of the electro-stimulation components extend, namely the retractable connection extensions (24) and the connection elements (14). It is to be noted that in a variation of the system, the retractable connection extensions (24) may directly lead to a respective stimulating end (12) in a non-disconnectable manner.

Various mechanical arrangements are possible to adjust the length of the connection extensions (24) depending on the patient-dependent particular auricular surface form of a given person, for instance by means of a slider mechanism by which an additional portion of the connection extension (24) is allowed to be slid out from the protective housing portion in which it is stored. A metallic ground surface contact area is provided on the ear-wearable body (26) of the device. The ground electrode therefore closes the loop for the electrical current. It can be a small conductive contact or a pad with several $cm^2$ area. The ground electrode connection can alternatively be at the back of the ear, neck, scalp, or other places in the proximity of the electrode. On the other hand, in the case of a plurality of active electrodes effecting stimulation, one of the active electrodes can be used as the cathode electrode or a pair of anode and cathode electrodes can reach each muscle. Alternatively, the cathode and anode electrodes can also be on different muscles.

In a preferred variation of the system, the function of location verification of auricular muscles can be performed by means of a peripheral unit in the form of a video capturing peripheral that collects blinking data of the patient by way of continuously monitoring the blinking activity of his/her eyes. When a person blinks his/her eyes, typically, a respective signal is generated and carried via the auricular muscles, such signal being specifiable by means of the EMG sensor embedded to the stimulating end (12) of the electro-stimulation device (10) or the ear-wearable device (23), detecting the respective signals and as such verifying identification of the intrinsic auricular muscles such as helicis major muscles, helicis minor muscles, tragicus muscles, anti-tragicus muscles, thereby verifying the accurate position of the stimulating end (12) and the EMG sensor (27) capturing the verification signal.

However, it is to be noted that accurate identification of the intrinsic auricular muscles at the very beginning of the treatment procedure when the electro-stimulation device (10) or the ear-wearable device (23) is operatively connected for the first time does not allow accurate adjustment of the threshold of the stimulating signal to be applied to said intrinsic auricular muscles. The threshold of the stimulating signal is a patient-dependent value and can even change throughout the day for a given patient. Therefore, the threshold of the stimulating signal must be accurately specified each time the electro-stimulation device (10) or the ear-wearable device (23) is to be activated.

Therefore, the peripheral unit in the form of a video capturing peripheral that collects blinking data and in signal communication with the control unit (21), in cooperation with the EMG sensor, verifies that the stimulating ends (12) are accurately positioned in the intrinsic auricular muscles when the blinking activity is detected by the video capturing peripheral (i.e. a camera) and the associated synchronized signal is detected by the EMG sensor (27); but the threshold of the stimulating signal must be separately specified by incrementally adjusting the same. When a stimulating signal as a voltage or current signal and preferably in the form of current-amplified signal is applied to the intrinsic auricular muscles, the reading state of the electro-stimulation device (10) or the ear-wearable device (23) is activated during which a corresponding muscle signal can be sensed by the EMG sensor in response to the stimulating signal. When a corresponding signal in return is received, threshold of the stimulating signal as a patient-specific and time-dependent value can be determined.

It is to be noted that proper values and preferable operational range of the threshold signal can be specified without using the video capturing peripheral because a return signal per se also verifies that the intrinsic auricular muscles are accurately located. However, use of the video capturing peripheral is advantageous in that it verifies identification of the intrinsic auricular muscles more practically in the absence of the effective threshold information, i.e. at the very beginning of the treatment procedure. Other than this, it is also advantageous during the incremental threshold calibration stage in that it differentiates natural blinking reflex and associated auricular muscle responses of a patient from the induced auricular muscle responses by the electro-stimulation device (10) or the ear-wearable device (23).

In a more specific manner, if a patient blinks his/her eyes during the incremental threshold calibration stage, it cannot be directly verified whether the intrinsic auricular muscle responses are caused by the natural blinking reflex of the patient or are only induced in response to the incrementally adjusted stimulation signal. To this end, although repetitive application of a certain number of specific threshold signal will be sufficient in practice in order for differentiating natural and induced auricular muscle responses, the video capturing peripheral facilitates this procedure and the auricular muscles' natural responses can be directly ignored if such responses are synchronized with natural blinking activity. In this case, an incrementally adjusted threshold value is ignored as it coincides with natural blinking movement as detected by the video capturing peripheral.

In sum, the procedure is performed such that the applied threshold value is gradually increased during a so-called stimulation state followed by an idle reading state during which the EMG sensor (27) remains ready to observe the auricular muscles' activity.

In a nutshell, the system provides an electro-stimulation device (10) comprising a plurality of electrodes (11) in communication with a control unit (21), the electrodes (11) being effective in enabling sending and receiving of electric signals in order to stimulate supplementary motor area, cerebellum, premotor area and/or subthalamic nucleus of a human. These electrodes (11) are attached to intrinsic auricular muscles such as helicis major muscles, helicis minor muscles, tragicus muscles and anti-tragicus muscles. The signal for stimulating the supplementary motor area, cerebellum, premotor area and/or subthalamic nucleus is produced by the control unit (21) and fed directly to the electrodes (11). In a preferred embodiment, different electro-stimulation devices (10) can be placed on the aforementioned locations on the left and right ear of the patient. Different muscles can be stimulated selectively at respective times. The ground electrode closes the loop for the electrical current by providing an electrical path to the negative terminal of the power supply.

Alternatively, an additional video capturing peripheral can enable receiving of images from the patient and hence enabling visual monitoring of symptoms such as tremors. The received images are then processed by known image processing techniques and information such as intensity of tremors is acquired.

An inertial measurement unit as a peripheral unit with an accelerometer can be attached to the limb of the patient, the activity of which is to be periodically monitored. Therefore, the intensity of disturbances can be sensed by measuring the acceleration of the limb. Upon measurement of the disturbance level, the stimulation signal can be adjusted to target the specific needs of a patient, i.e. so as to be adapted to the changing state of the patient.

The adjustments to the stimulation signal can typically be carried out by changing the amplitude, frequency, pulse width, and pulse shape such as the harmonic content of the periodic pulses etc. The phases of the electro-stimulating devices (10) relative to each other can be adjusted if a multitude of electro-stimulating devices (10) are used.

The electro-stimulation device (10) typically comprises a communication unit in signal communication with the control unit (21), enabling communication with other devices such as remote control units, computers, peripheral measurement/sensor units etc. The communication unit conventionally supports known communication protocols/standards (IR, USB, IEEE 802 family, Bluetooth, RF communication interface, RS-232, RS-422, RS-485, SPI (serial peripheral interface) i2c, as well as proprietary interfaces and/or protocols etc.).

This driving circuit typically enables driving power levels greater than the control unit (21). Therefore, power can be fed to the electrodes (11) by the driving circuit.

In the preferred embodiment, different stimulating signal parameters (voltage, current, signal period, polarization and signal form) can be adjusted and the signal produced by the control unit (21) may have a voltage of 0V-15V and the frequency of 2 Hz-250 Hz. The parameters of the stimulating signal can be automatically changed by the control unit (21) depending on the situation of the patient or they can be remotely changed via a remote unit by an authorized user such as a physician, upon evaluating the situation of the patient. The frequency of the stimulation signals being generated is preferably between 2-250 Hz. It is worthy of note that lower limit of said frequency is selected as 2 Hz because 2 Hz is found to be a frequency value that induces peripheral nerve regeneration by protecting and regenerating the biological stimulation pathway, the axons elongated from the intrinsic auricular muscles to the muscle coordination related brain structures.

In a variation of the system, two electro-stimulation devices (10) or ear-wearable devices (23) are simultaneously operated for both ears of a patient in synchronized manner as the present inventors have found that stimulation of intrinsic auricular muscles at both sides in a synchronized manner synergistically induce positive results associated with the treatment, which is primarily found to be related to the intrinsic auricular muscles, which constitute the only regressed (not actively used in adulthood) muscle group, stimulation of which effect supplementary motor area, premotor area, subthalamic nucleus and cerebellum simultaneously in both lobes of the brain.

In a further variation of the system, the electro-stimulation device (10) also monitors frequency and wavelength of the applied voltage or current electrical signal through the driving circuit, which is advantageous in that the driving circuit in electrical connection with a feedback loop ensures that no variations occur in the stimulation signal during the stimulating states of subsequent periods of the stimulation signal.

In a further variation of the system, the control unit (21) is preferably integral with the electro-stimulation device (10) and can be controlled by a remote terminal through an appropriate software module to adjust parameters of the stimulation procedure.

In a further variation of the system, the stimulation signal can include signal components in the bursting frequencies. As is known to the skilled worker, bursting is a phenomenon of neuron activation patterns where periods of rapid action potential spiking are followed by resting phase periods.

FIG. 3 additionally demonstrates an additional electrode (shown by dashed lines) reaching to a fourth intrinsic auricular muscle group.

In one embodiment, an electro-stimulation device (10) comprising at least one electrode (11) is proposed, said at least one electrode (11) being provided with a stimulation end (12) configured to stimulate intrinsic auricular muscles of a human, said stimulation end (12) being operatively coupled with a sensor (27).

In a further embodiment, the stimulation end (12) of said electrode (11) is adapted to generate an electrical stimulating signal during a stimulating state of a signal and said sensor (27) is adapted to detect an electrical signal generated in an intrinsic auricular muscle during the contraction thereof and at rest during a reading state of the same period other than the stimulating state and, In a still further embodiment, a control unit (21) of the electro-stimulation device (10) is configured to gradually change the electrical stimulating signal applied by the stimulation end (12) during stimulating states of subsequent periods of the signal and to determine at least one electrical stimulating signal value in response to which an electrical signal is generated in an intrinsic auricular muscle during at least one reading state of subsequent periods of the signal.

In a yet still further embodiment, said sensor is an EMG sensor (27).

In a yet still further embodiment, said stimulation end (12) is configured to be directly attached to intrinsic auricular muscles so as to establish a direct contact relation therewith.

In a yet still further embodiment, said stimulation end (12) is configured to stimulate intrinsic auricular muscles at a position on the external portion of the human ear closest to said intrinsic auricular muscles. Although this arrangement may cause skin irritations depending on the patient, it is possible to determine an alternative set of threshold stimulation signal values by applying the stimulation signals directly on the external portion of the ear.

In a yet still further embodiment, said intrinsic auricular muscles with which said stimulation end (12) is configured to stimulate include at least one of the helicis major muscles, helicis minor muscles, tragicus muscles, anti-tragicus muscles.

In a yet still further embodiment, electrical stimulating signal parameters include sign, amplitude, frequency, signal period, signal form, harmonic content and pulse width of voltage and/or current.

In a yet still further embodiment, the EMG sensor (27) measures electrical current impulses generated in the intrinsic auricular muscles.

In a yet still further embodiment, different time slots are allocated for the stimulating signal during stimulating state of a signal period and for the signal generated in an intrinsic auricular muscle during a reading state of a signal period.

In a yet still further embodiment, said electrodes (11) are configured to be in the form of needle-shaped electrodes (11) enclosed by an insulating sleeve (13) apart from the stimulation ends (12) thereof.

In a yet still further embodiment, said electro-stimulation device (10) comprises a connection element (14) detachably connected to an electrode (11).

In a yet still further embodiment, said connection element (14) comprises an enclosure (16) and a receiving portion (15) adapted to receive the longitudinally extending core (20) of the electrode (11).

In a yet still further embodiment, polarity of the stimulating signal is adjusted by applying positive and negative signals in consecutive periods.

In a yet still further embodiment, the stimulation end (12) is provided with an annular flange as a retainment portion (22) extending over the cross-sectional area of the tubular-form insulating sleeve (13).

In a yet still further embodiment, operational position of the core (20) of the electrode (11) being introduced to the receiving portion (15) is maintained by a magnetic element (18) placed on said connection element (14) and a magnetic anchoring means (19) placed on the electrode (11) such that the connection element (14) is securely connected and removably coupled to the electrode (11).

In a yet still further embodiment, as an alternative arrangement, operational position of the core (20) of the electrode (11) being introduced to the receiving portion (15) is maintained through application of negative pressure by means of said enclosure (16) as a suction cup such that the connection element (14) is securely connected and removably coupled to the electrode (11).

In a yet still further embodiment, at least one thermal or pressure sensor in signal communication with the control unit (21) is provided to externally determine accurate location of the intrinsic auricular muscles.

In a yet still further embodiment, a laser marking system is provided to indicate accurate location of the intrinsic auricular muscles.

In a yet still further embodiment, a video capturing peripheral in signal communication with the control unit (21) is provided to collect blinking data of a patient by way of continuously monitoring the blinking activity thereof.

In a yet still further embodiment, the control unit (21) processes data collected by the video capturing peripheral such that natural blinking movements of a patient are differentiated from blinking movements induced by the stimulating signal whereby at least one threshold value of the stimulating signal is determined in view of the natural blinking movements being ignored.

In a yet still further embodiment, values of electrical stimulating signal parameters are selectively varied according to data collected by at least one of peripheral sensing units including an inertial measurement unit, a voice recording unit or an image capturing unit.

In a yet still further embodiment, the inertial measurement unit with an accelerometer in signal communication with the control unit (21) is provided to collect movement data from a human limb being attached thereto.

In a yet still further embodiment, a voice recording unit in signal communication with the control unit (21) is provided to monitor voice parameters including intensity, speed and swallowing duration of a patient.

In a yet still further embodiment, voice parameters including intensity, speed and swallowing duration are analyzed real-time or as a pre-recorded sample.

In a yet still further embodiment, an image capturing unit in signal communication with the control unit (21) is provided to capture images from different body portions or extremities of a patient to detect symptoms such as tremors.

In a yet still further embodiment, said electro-stimulation device (10) is an ear-wearable device (23) with a plurality of stimulating ends (12), each of which being equipped with an EMG sensor (27) operatively coupled thereto.

In a yet still further embodiment, said ear-wearable device (23) the connection elements (14) of which are releasably couplable to the stimulating ends (12) during operation of the device.

In a yet still further embodiment, said ear-wearable device (23) comprises flexible and/or retractable connection extensions (24) to adjust the distance between a connection element (14) releasably connectable with a stimulating end (12) and a housing portion (25) of the ear-wearable device (23).

In a yet still further embodiment, said electro-stimulation device (10) is mountable to or integral with a hearing aid.

In a yet still further embodiment, the signal produced by the control unit (21) has a voltage of 0V-15V and the frequency thereof is between 2 Hz-250 Hz.

In a yet still further embodiment, two electro-stimulation devices (10) are operable in a simultaneous manner in the manner that the electrical stimulating signal generated during a stimulating state is applied by said two electro-stimulation devices (10) at both ears in a synchronized manner.

In a yet still further embodiment, the electro-stimulation device (10) comprises a temperature sensor such that temperature of the stimulation end (12) is continuously monitored to avoid excessive heating thereof beyond a predetermined limit.

In a yet still further embodiment, the device such that the stimulation end's (12) initial temperature and temperature thereof at the end of a predetermined inactive period prior to the stimulation, indicative of the temperature of a respective intrinsic auricular muscle are monitored and the active state temperature of the stimulation end (12) is intermittently decreased to the temperature of the respective intrinsic auricular muscle as measured at the end of a predetermined inactive period of the stimulation end (12).

In a yet still further embodiment, frequency and wavelength of the applied electrical stimulating signal is continuously monitored through a driving circuit in electrical connection with a feedback loop to ensure that no variations occur in the stimulation signal during the stimulating states of subsequent periods of the stimulation signal.

In a yet still further embodiment, the control unit (21) is preferably integral with the electro-stimulation device (10).

In a yet still further embodiment, one of the electrodes is used as the cathode electrode and the cathode and anode electrodes are on the same or different muscles.

In a yet still further embodiment, the stimulating signal includes signal components in the bursting frequencies.

The previously described embodiments, alternative embodiments and variations may be used/implemented independently or in any combination with each other, unless otherwise indicated. Thus, it should be understood that within the electro-stimulation system the features and functionality described for one or more embodiments, alternative embodiments or variations may be combined with the features and functionality of other of the one or more embodiments, alternative embodiments or variations. In addition, it should be understood that the features and functionality described for one or more embodiments, alternative embodiments or variations may be modified to include features and functionality of other of the one or more embodiments, alternative embodiments or variations for purposes of cooperative operation/functionality.

The methods, devices, processing, circuitry, and logic described above for the electro-stimulation system may be implemented in many different ways and in many different combinations of hardware and software. For example, all or parts of the implementations of the electro-stimulation device (10), the driving circuit, the communication unit, the control unit (21) or other components within the system may be circuitry that includes an instruction processing unit or processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical data storage medium; or in or on another machine-readable medium that is other than transitory. A product, such as a computer program product, may include a storage medium and instructions stored in or on the medium, and the instructions when executed by the circuitry in the system or device may cause device(s) in the system to implement any of the processing described above or illustrated in the drawings.

Various example embodiments have been described. These and other examples are within the scope of the following claims.

The invention claimed is:

1. An electro-stimulation device comprising:
a control circuitry and at least one electrode, said at least one electrode including a stimulation end configured to stimulate intrinsic auricular muscles of a human, said stimulation end operatively coupled with a sensor;
wherein, the stimulation end of said at least one electrode is adapted to generate an electrical stimulating signal during a stimulating state of a cycle period, and said sensor is adapted to detect an electrical signal generated in an intrinsic auricular muscle during contraction and at rest, the detection during a reading state of the cycle period that is other than during the stimulating state,
wherein the control circuitry of the electro-stimulation device configured to change the electrical stimulating signal applied by the stimulation end during stimulating states of subsequent cycle periods and to determine at least one electrical stimulating signal value in response to which the electrical signal is generated in the intrinsic auricular muscle during at least one reading state of subsequent cycle periods,
said at least one electrode comprises an insulating sleeve surrounding said at least one electrode except for the stimulation end such that said insulating sleeve is configured for placement between an ear skin surface and under a skin muscular tissue area and said at least one electrode is configured to prick the ear skin surface so the stimulation end of the at least one electrode reaches said intrinsic auricular muscles, and
a connection element detachably connected to the at least one electrode, wherein said connection element comprises an enclosure and a receiving portion adapted to receive a longitudinally extending core of the at least one electrode,
wherein the core of the at least one electrode being introduced to the receiving portion is maintained by a magnetic connection between a magnetic element on said connection element and a magnetic anchoring means on the core of the at least one electrode such that the connection element is securely connected and removably coupled to the at least one electrode.

2. The electro-stimulation device as in claim 1, wherein said sensor is an electromyography (EMG) sensor.

3. The electro-stimulation device as in claim 2, wherein the EMG sensor measures electrical current impulses generated in the intrinsic auricular muscle.

4. The electro-stimulation device as in claim 1, wherein said stimulation end is configured to be directly attached to intrinsic auricular muscles so as to establish a direct contact relation therewith.

5. The electro-stimulation device as in claim 4, wherein said intrinsic auricular muscles with which said stimulation end is configured to stimulate at least one of helicis major muscles, helicis minor muscles, tragicus muscles, anti-tragicus muscles, or any combination thereof.

6. The electro-stimulation device as in claim 4, wherein different time slots within the cycle period are allocated by the control circuitry for generation of the electrical stimulating signal during the stimulating state and for sensing the electrical signal generated in an intrinsic auricular muscle during the reading state.

7. The electro-stimulation device as in claim 4, wherein said at least one electrode is configured to be in a form of a needle-shaped electrode enclosed by said insulating sleeve apart from the stimulation end thereof.

8. The electro-stimulation device as in claim 5, wherein parameters of the electrical stimulating signal include sign, amplitude, frequency, cycle period, signal form, harmonic content and pulse width of voltage and/or current.

9. The electro-stimulation device as in claim 8, wherein a polarity of the electrical stimulating signal is adjusted by the control circuitry by application of positive or negative signals during the stimulating state in consecutive cycle periods.

10. The electro-stimulation device as in claim 8, further comprising at least one peripheral sensing unit in communication with the control circuitry, wherein values of electrical stimulating signal parameters are selectively varied by the control circuitry according to data collected by the at least one peripheral sensing unit, wherein the at least one peripheral sensing unit comprises an inertial measurement unit, a voice recording unit, an image capturing unit or a combination thereof.

11. The electro-stimulation device as in claim 10, wherein the inertial measurement unit further comprises an accelerometer in signal communication with the control circuitry, the accelerometer configured to be attached to a human limb and supply movement data of the human limb to the control circuitry.

12. The electro-stimulation device as in claim 10, wherein the voice recording unit in signal communication with the control circuitry is configured to monitor, in real-time or as a pre-recorded sample, voice parameters including intensity, speed and swallowing duration of a patient.

13. The electro-stimulation device as in claim 10, wherein the image capturing unit in signal communication with the control circuitry is configured to capture images from different body portions or extremities of a patient to detect symptoms, the symptoms comprising tremors.

14. The electro-stimulation device as in claim 1, wherein said stimulation end is configured to stimulate intrinsic auricular muscles at a position on an external portion of a human ear closest to said intrinsic auricular muscles.

15. The electro-stimulation device as in claim 1, wherein the stimulation end includes an annular flange as a retainment portion extending over a cross-sectional area of a tubular portion of the insulating sleeve, the annular flange configured to retain the insulating sleeve between the ear skin and the stimulation end in the skin muscular tissue area.

16. The electro-stimulation device as in claim 1, further comprising at least one thermal or pressure sensor in signal communication with the control circuitry and configured to externally determine a location of the intrinsic auricular muscles.

17. The electro-stimulation device as in claim 16, further comprising a laser marking system configured to indicate the location of the intrinsic auricular muscles.

18. The electro-stimulation device as in claim 1, further comprising a video capturing peripheral in signal communication with the control circuitry and configured to collect blinking data of a patient by continuous monitoring of blinking activity of the patient.

19. The electro-stimulation device as in claim 18, wherein the control circuitry is configured to process data collected by the video capturing peripheral such that natural blinking movements of the patient are differentiated from blinking movements of the patient induced by the stimulating signal, wherein the control circuitry is configured to determine at least one threshold value of the stimulating signal by ignoring the natural blinking movements.

20. The electro-stimulation device as in claim 1 wherein said electro-stimulation device is an ear-wearable device with a plurality of stimulating ends operatively coupled with an electromyography (EMG) sensor.

21. An electro-stimulation device as in claim 20, wherein said ear-wearable device comprises a plurality of connection elements which are releasably couplable to the stimulating ends during operation.

22. An electro-stimulation device as in claim 20, wherein the at least one electrode comprises a pair of electrodes, one of the pair of electrodes configured as a cathode electrode and another of the pair of electrodes configured as an anode electrode, the cathode and anode electrodes being positionable on a same intrinsic auricular muscle or different intrinsic auricular muscles.

23. An electro-stimulation device as in claim 21, wherein said ear-wearable device comprises flexible and/or retractable connection extensions to adjust a distance between the connection elements releasably coupleable to the stimulating ends and a housing portion of the ear-wearable device.

24. An electro-stimulation device as in claim 1, wherein said electro-stimulation device is mountable to or integral with a hearing aid.

25. An electro-stimulation device as in claim 1, wherein the control circuitry is configured to generate the electrical stimulating signal, and the electrical stimulating signal has a voltage of 0V-15V and a frequency of the cycle period between 2 Hz-250 Hz.

26. An electro-stimulation device as in claim 1, further comprising a temperature sensor, the control circuitry configured to continuously monitor a temperature of the stimulation end with the temperature sensor to avoid excessive heating thereof beyond a predetermined limit.

27. An electro-stimulation device as in claim 26, wherein the control circuitry is configured to monitor, with the temperature sensor, a temperature at an end of a predetermined inactive period prior to the stimulating state, the temperature at the end of the predetermined inactive period being indicative of a temperature of a respective intrinsic auricular muscle, and the control circuitry is further configured to intermittently decrease an operating temperature of the stimulation end to the temperature of the respective intrinsic auricular muscle as measured at the end of the predetermined inactive period of the stimulation end.

28. An electro-stimulation device as in claim 1, wherein the control circuitry is configured to continuously monitor a frequency and a wavelength of the applied electrical stimulating signal through a driving circuit in electrical connection with a feedback loop to ensure that no variations occur in the electrical stimulation signal during the stimulating states of subsequent cycle periods of the electrical stimulation signal.

29. An electro-stimulation device as in claim 1, wherein the control circuitry is integral with the electro-stimulation device.

30. An electro-stimulation device as in claim 1, wherein the stimulating signal includes signal components in bursting frequencies.

31. An electro-stimulation system comprising:
a first electro-simulation device and a second electro-stimulation device, each of the first and second electro-simulation devices comprising:
a control circuitry and at least one electrode, said at least one electrode including a stimulation end configured to stimulate intrinsic auricular muscles of a human, said stimulation end operatively coupled with a sensor;
wherein, the stimulation end of said at least one electrode is adapted to generate an electrical stimulating signal during a stimulating state of a cycle period, and said sensor is adapted to detect an electrical signal generated in an intrinsic auricular muscle during contraction and at rest, the detection during a reading state of the cycle period that is other than during the stimulating state,
wherein the control circuitry of the electro-stimulation device is configured to change the electrical stimulating signal applied by the stimulation end during stimulating states of subsequent cycle periods and to determine at least one electrical stimulating signal value in response to which the electrical signal is generated in the intrinsic auricular muscle during at least one reading state of subsequent cycle periods,
said at least one electrode comprises an insulating sleeve surrounding said at least one electrode except for the stimulation end such that said insulating sleeve is configured for placement between an ear skin surface and under a skin muscular tissue area and said at least one electrode is configured to prick the car skin surface so the stimulation end of the at least one electrode reaches said intrinsic auricular muscles,
a connection element detachably connected to the at least one electrode, wherein said connection element comprises an enclosure and a receiving portion adapted to receive a longitudinally extending core of the at least one electrode, wherein the core of the at least one electrode being introduced to the receiving portion is maintained by a magnetic connection between a magnetic element on said connection element and a magnetic anchoring means on the core of the at least one electrode such that the connection element is securely connected and removably coupled to the at least one electrode; and
wherein the control circuitry of the first electro-stimulation device and the control circuitry of the second electro-stimulation device are operable in a simultaneous manner, such that the electrical stimulating signal respectively generated by the first and second electro-stimulation devices during a stimulating state are respectively applied at both ears of the human in a synchronized manner.

* * * * *

UNITED STATES PATENT AND TRADEMARK OFFICE
CERTIFICATE OF CORRECTION

| | |
|---|---|
| PATENT NO. | : 11,247,047 B2 |
| APPLICATION NO. | : 16/125416 |
| DATED | : February 15, 2022 |
| INVENTOR(S) | : Yusuf Ozgur Cakmak et al. |

It is certified that error appears in the above-identified patent and that said Letters Patent is hereby corrected as shown below:

In the Claims

Column 16, Claim 31, Line 35, delete "car" and insert in its place --ear--.

Signed and Sealed this
Fifth Day of July, 2022

Katherine Kelly Vidal
*Director of the United States Patent and Trademark Office*